United States Patent [19]

Markofsky

[11] Patent Number: 4,933,464

[45] Date of Patent: Jun. 12, 1990

[54] PROCESS FOR FORMING 3-PHENYLISOXAZOLINES AND 3-PHENYLISOXAZOLES

[75] Inventor: Sheldon B. Markofsky, Olney, Md.

[73] Assignee: W. R. Grace & Co.-Conn., New York, N.Y.

[21] Appl. No.: 185,616

[22] Filed: Apr. 25, 1988

[51] Int. Cl.$^5$ .................. C07D 261/04; C07D 261/08; C07D 261/10; C07D 261/12

[52] U.S. Cl. ..................... 548/247; 548/240; 548/243; 548/244; 548/245; 548/248; 548/249

[58] Field of Search ............... 548/240, 243, 244, 245, 548/247, 248, 249

[56] References Cited

U.S. PATENT DOCUMENTS

| | | | |
|---|---|---|---|
| 3,945,998 | 3/1976 | Anderson et al. | 546/275 |
| 4,092,326 | 5/1978 | Shipchandler | 548/237 |
| 4,479,888 | 10/1984 | Koch et al. | 548/335 |
| 4,670,109 | 6/1987 | Delay et al. | 548/247 |

FOREIGN PATENT DOCUMENTS 103070  5/1987  Japan .................. 548/240

OTHER PUBLICATIONS

Huisgen, *Angew. Chem. Intl. Ed.*, vol. 2, No. 10, pp. 565, 573–575 (1963).
"Phase Transfer Catalysis" by Starks et al., Academic Press, pp. 162–163 (1978).
Rahman et al. *Chemical Abstracts*, vol. 101, No. 54969v (1984).
Abstract for JP No. 103070 (5/13/87).
Kornblum et al., J.A.C.S. 80, 4333, (1958).

*Primary Examiner*—Anton H. Sutto
*Assistant Examiner*—E. Bernhardt
*Attorney, Agent, or Firm*—Howard J. Troffkin

[57] ABSTRACT

A one-step process to form 3-phenylisoxazolines and 3-phenylisoxazoles by contacting a benzyl halide, a nitrite and an olefin or acetylenic compound, respectively, in the presence of a phase transfer agent.

15 Claims, No Drawings

PROCESS FOR FORMING 3-PHENYLISOXAZOLINES AND 3-PHENYLISOXAZOLES

BACKGROUND OF THE INVENTION

The present invention is directed to a one-step reaction to produce 3-phenylisoxazolines and 3-phenylisoxazoles. More particularly, the invention is directed to contacting a benzyl halide and sodium nitrite with an alpha-olefin to provide the isoxazoline or with an acetylene to provide the isoxazole in good yields.

Isoxazolines and isoxazoles have a wide variety of uses. They are useful as intermediates in pharmaceutical applications and application in flavor and fragrance chemistry and as water treatment agents.

The subject compounds are presently formed by synthetic routes which require several steps and difficult operating conditions. For example, the common method of forming 3-phenylisoxazolines involves the initial reaction between benzaldehyde and hydroxylamine hydrochloride to form an oxime. The oxime is treated with an alkali hypochlorite to form the oximochloride which is then reacted with an olefin in the presence of base to provide the phenylisoxazoline. 3-phenylisoxazoles were similarly formed using acetylenes in place of the olefin. A less complex synthesis to provide the subject products is highly desired.

SUMMARY OF THE INVENTION

The present invention is directed to a one-step process for forming 3-phenylisoxazolines and 3-phenyl isoxazoles. The process comprises substantially simultaneously contacting a benzyl halide with a nitrite salt and with a compound containing an olefinic or acetylenic unsaturation in the presence of a phase transfer agent. The product so formed is a 3-phenylisoxazoline or a 3-phenyl-5-substituted isoxazoline when an olefinic reactant is used and a 3-phenylisoxazole or a 3-phenyl-5-substituted isoxazole when an acetylenic reactant is used.

DETAILED DESCRIPTION OF THE INVENTION

The present process requires contacting a benzyl halide with a nitrite and with a compound containing olefinic or acetylenic unsaturation in the presence of a phase transfer agent, as described in detail hereinbelow.

The benzyl halide useful in the present process can be selected from compounds represented by the general formula

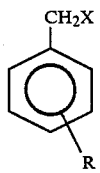

wherein X represents a halogen atom such as chlorine, bromine and the like with chlorine being preferred and R represents any group which is inert to the reaction conditions, such as, hydrogen or a $C_1$–$C_{10}$ (preferably a $C_1$–$C_5$) alkyl or substituted alkyl group such as methyl, ethyl, propyl, hydroxymethyl, hydroxyethyl, methoxy and the like. The alkyl or substituted alkyl group can be substituted for a hydrogen atom of any aromatic carbon. Examples of benzyl halides compounds suitable for the present process include benzyl chloride, benzyl bromide, ortho, meta or para-methylbenzyl chloride, ortho, meta or para-hydroxymethylbenzyl chloride, ortho, meta or para-methoxybenzyl chloride, and the like. The particular benzyl halide used will be dependent on the product desired. These compounds are commercially available or can be readily synthesized by known means.

The nitrite salt can be selected from an alkali metal nitrite with sodium nitrite being preferred due to its ready availability and low cost. Other suitable nitrites include alkaline earth metal nitrite such as calcium nitrite and the like; tetraalkyl phosphonium nitrite or tetraalkyl ammonium nitrite in which the alkyl group may be independently selected from a $C_1$–$C_{20}$ alkyl as, for example, tetrabutyl ammonium nitrite and the like. The nitrite salt may be supplied as a single salt or as a mixture of such salts.

When the supplied nitrite salt is a phosphonium or ammonium salt, the present process does not require the presence of additional phase transfer agent as described below. The phosphonium and ammonium nitrites act as both the source of the nitrite reactant and as the phase transfer agent.

The unsaturated compound required in the present process can be either an olefinic or acetylenic compound. The former compound yields the subject isoxazolines while the later yields the isoxazole. Olefinic compounds which are useful can be represented by the formula ZCH=CHY wherein each Z and Y is independently selected from a group which is inert with respect to the subject reaction and, for example, can be hydrogen, and alkyl such as methyl, ethyl, propyl, amyl and the like with $C_1$–$C_5$ being preferred; carboxylic acid ester; carboxylic acids; halogens such as chloro, bromo and the like; ethers, such as methoxy, ethoxy, phenoxy and the like; tertiary amino groups such as dimethylamino, diethylamino and the like; phenyl and substituted phenyl groups as well as a nitro group, a nitrile group, an acetate or the like. The alkyl and phenyl groups may be substitued with ester, halo or other groups which are substantially inert to the present reagents and conditions. It is preferred that at least one of the Z and Y groups be hydrogen, that is, that the preferred olefin is an alpha olefin. Examples of suitable olefinic compounds include propylene, 1-butene, 1-pentene, vinyl acetate, dimethyl maleate, diethyl maleate, diethyl fumarate, vinyl methyl ether and the like. The particular dipolarophile used will be determined by the particular product desired.

When the unsaturated compound is selected from an olefinic compound as described above, one attains a 3-phenyl isoxazoline represented by the general formula:

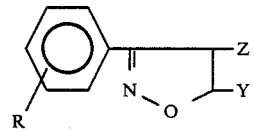

in which R, Z and Y represent groups as described above.

The dipolarophile can be selected from an acetylenic compound having the general formula Z-C≡C-Y in which Z and Y are each independently selected from groups Z and Y as defined above with respect to the olefinic compound. When the dipolarophile is an acetylenic compound, the resultant product will be an isoxazole represented by the general formula:

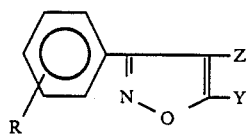

with R, Z and Y representing the groups described above.

The reaction is carried out by contacting all of the above reactants together in a liquid media. The liquid media can be any liquid which is inert to the reaction and the reactants and in which the reactants exhibit some solubility. The liquid can be excess benzyl halide or excess of alpha-olefin provided it is liquid under reaction conditions (the excess by definition not taking part in the reaction). The liquid media may be a hydrocarbon such as pentane, heptane, hexane, decane, benzene, toluene and the like; ethers such as dimethyl ether, diethyl ether, tetrahydrofuran and the like; sulfoxides such as dimethyl sulfoxide and the like. It is preferred that the reaction media be excess benzyl halide in order to simplify the reaction and the separation of the product therefrom.

The reaction can be carried out under temperatures ranging from ambient to elevated such as about 200° C. Higher or lower temperatures may be used to provide a liquid media while proceeding with the reaction. The pressure of the reaction zone can be atmospheric pressure or elevated. Elevated pressure is required where the reactants have boiling points or high vapor pressure at the reaction temperature used. The exact amount of pressure needed will, therefore, depend on the reactants used. It is preferred that the reaction be conducted at autogenous pressure in a closed vessel.

The reactants are contacted in the presence of a phase transfer agent such as cyclic ethylene oxide compounds conventionally known as crown ethers as, for example, 18-crown-6, 16-crown-5 (the first number represents total atoms and second number represents oxygen atoms of the cyclic compound) and the like, low molecular weight polyethyleneoxide (MW=200-4000) as well as tetraalkyl phosphonium halides, tetraalkyl ammonium halides and the like.

The reaction mixture is agitated for a period of time sufficient to provide the product in good yields. The period needed can be readily determined in manners known to those skilled in this art. The reaction period normally ranges from 1 hr to 200 hrs. The product can be separated by known means including distillation, precipitation, flash chromatography or other means deemed applicable to the artisan.

The following example is given for illustrative purposes only and is not meant to be a limitation on the invention as defined by the claims appended hereto. All parts and percentages are by weight unless otherwise indicated.

8.90 parts of benzyl chloride, 3.27 parts sodium nitrite, 5.89 parts 1-hexene and 1 part of 18-crown-6 (cyclic ethylene oxide) were contacted together and agitated at room temperature for 140 hours. The product, 3-phenyl-5-butylisoxazoline, was identified by gas chromatography/mass spectral data. The yield of product was approximately 50 percent based on the benzyl chloride charge.

What is claimed:

1. A process for forming a product selected from an isoxazoline having the formula:

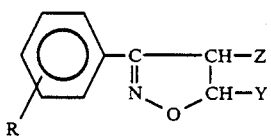

or an insoluble of the formula:

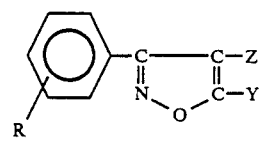

comprising contacting a benzyl halide represented by the formula:

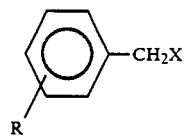

with an unsaturated compound selected from an olefinic compound of the formula ZHC=CHY to form compound I or an acetylenic compound of the formula ZC≡CY to form compound II and with a nitrite salt in the presence of a phase transfer agent in a liquid medium in which the reactants exhibit some solubility and recovering the resultant product; wherein the nitrite salt is selected from alkali metal nitrite, alkaline earth metal nitrite, tetraalkyl phosphonium nitrite and tetraalkyl ammonium nitrite and mixtures thereof, the phase transfer agent is selected from a cyclic ethylene oxide, a low molecular weight polyalkylene oxide, tetraalkyl phosphonium halide and tetraalkyl ammonium halide and mixtures thereof and in each of the above formula each R represents hydrogen or a $C_1$-$C_{10}$ alkyl or substituted alkyl group, X represents a halogen atom, and each Y and Z independently represents a group which is inert with respect to the reactants and the subject reaction.

2. The process of claim 1 wherein the reaction is carried out at from about ambient to about 200° C.

3. The process of claim 2 wherein the liquid medium comprises an excess amount of one of the reactants over the stoichiometric amount required.

4. The process of claim 1 wherein the process is carried out at a temperature of from ambient to 200° C. and under autogenous pressure.

5. The process of claim 1 wherein each Y and Z independently represents a group selected from hydrogen, an alkyl, carboxylic acid ester, halogen, alkoxy, tertiary amino, nitro, nitrile and phenyl.

6. The process of claim 2 wherein the benzyl halide is benzyl chloride.

7. The process of claim 2 wherein the unsaturated compound is an olefin which is liquid under the reaction conditions.

8. The process of claim 7 wherein the olefin has hydrogen as an Z group and a $C_1$-$C_5$ alkyl as a Y group.

9. The process of claim 2 wherein the unsaturated compound is an acetylenic compound in which Z is hydrogen and Y is a $C_1$-$C_5$ alkyl.

10. The process of claim 1 wherein the nitrite salt is selected from an alkali or alkaline earth metal nitrite.

11. The process of claim 10 wherein the nitrite salt is an alkali metal nitrite.

12. The process of claim 1 wherein the nitrite salt is selected from a phosphonium nitrite or ammonium nitrite.

13. The process of claim 2 wherein the nitrite salt is selected from a phosphonium nitrite or ammonium nitrite.

14. The process of claim 3 wherein the excess reactant is benzyl chloride.

15. The process of claim 3 wherein the excess reactant is an olefin which is liquid under the reaction conditions.

* * * * *